(12) United States Patent
Risser

(10) Patent No.: US 8,674,126 B2
(45) Date of Patent: Mar. 18, 2014

(54) RUBIDIUM AND CESIUM COMPOUNDS FOR TWO-PHOTON ABSORPTION

(75) Inventor: Steven Risser, Reynoldsburg, OH (US)

(73) Assignee: Battelle Memorial Institute, Columbus, OH (US)

( * ) Notice: Subject to any disclaimer, the term of this patent is extended or adjusted under 35 U.S.C. 154(b) by 0 days.

(21) Appl. No.: 13/825,407

(22) PCT Filed: Sep. 27, 2011

(86) PCT No.: PCT/US2011/053415
§ 371 (c)(1),
(2), (4) Date: Mar. 21, 2013

(87) PCT Pub. No.: WO2012/044608
PCT Pub. Date: Apr. 5, 2012

(65) Prior Publication Data
US 2013/0178641 A1    Jul. 11, 2013

Related U.S. Application Data

(60) Provisional application No. 61/386,687, filed on Sep. 27, 2010.

(51) Int. Cl.
*C07F 5/06*   (2006.01)
*C07F 7/28*   (2006.01)
*C07F 9/00*   (2006.01)

(52) U.S. Cl.
USPC ............... 556/41; 556/44; 556/54; 556/55; 556/182; 556/183; 556/184; 556/482

(58) Field of Classification Search
USPC .......... 556/41, 44, 54, 55, 182, 183, 184, 482
See application file for complete search history.

(56) References Cited

U.S. PATENT DOCUMENTS 3,949,323 A   4/1976   Bierlein et al.
5,865,867 A   2/1999   Kinoshita

FOREIGN PATENT DOCUMENTS

EP   2 206 945      7/2010
JP   H 06-116097    4/1994

OTHER PUBLICATIONS

Bunge, S.D., et al., "Synthesis and Characterization of a Series of Rubidium Alkoxides and Rubidium-Titanium Double Alkoxides", Inorg. Chem., 2004, 43, pp. 6035-6041.
Chui, H., et al. "Absolute frquency measurement of rubidium 5s-7s two-photon transitions with a femtosecond laser comb", Optics Letters (Apr. 15, 2004) vol. 30, No. 8, pp. 842-844, 11 refs., Abstract.
Gorbunkov, M.V., et al., "Pulsed-diode-pumped, all-solid-state, electro-optically controlled picoseconds Nd:YAG lasers", Quantum Electronics, 35(1) 2-6 (2005).
Jackel, J., et al., "Ion-exchanged optical waveguides for all-optical switching", Applied Optics (1990), 29(21), pp. 3126-3129, Abstract.
Mataki, H. et al., "High-Gain Optical Amplification of Europium-Aluminum ($Eu^{3+}$-Al)-Nanocluster-Doped Planar Polymer Waveguides", Japanese Journal of Applied Physics, vol. 46, No. 3, 2007, pp. L83-L85.
Mehrotra, R.C., et al., "Synthesis of Apparently Covalent Double Alkoxides of Rubidium & Caesium", Indian Journal of Chemistry, vol. 14A, Nov. 1976, pp. 878-879.
Sargsyan, A., et al., "Narrow and contrast resonance of increased absorption in A-system observed in Rb cell with buffer gas", Aremenian Journal of Physics, 2009, vol. 2, issue 2, pp. 84-94.
English Machine Translation of Japanese Patent No. JP H 06-116097.
International Search Report for Application No. PCT/US2011/053415 dated Nov. 24, 2011.
International Preliminary Report on Patentability and Written Opinion for Application No. PCT/US2011/053415 dated Apr. 2, 2013.

*Primary Examiner* — Porfirio Nazario Gonzalez
(74) *Attorney, Agent, or Firm* — Frost Brown Todd LLC

(57) ABSTRACT

A material which electronically isolates a rubidium or cesium atom, which is bonded to only one or two oxygen atoms. This electronic isolation is manifested in narrow photoluminescence emission spectral peaks. The material may be an alkali metal compound comprises the empirical formula: $AM(R_1)(OR)_x$; where A is selected from Rb and Cs; M is selected from Al, Ti and V; each R is an independently selected alkyl or aryl group, $R_1$ is selected from alkyl alcohol, aryl alcohol, or a carboxyl group, where OR and $R_1$ are not the same, and x is 2, 3, or 4.

21 Claims, 5 Drawing Sheets

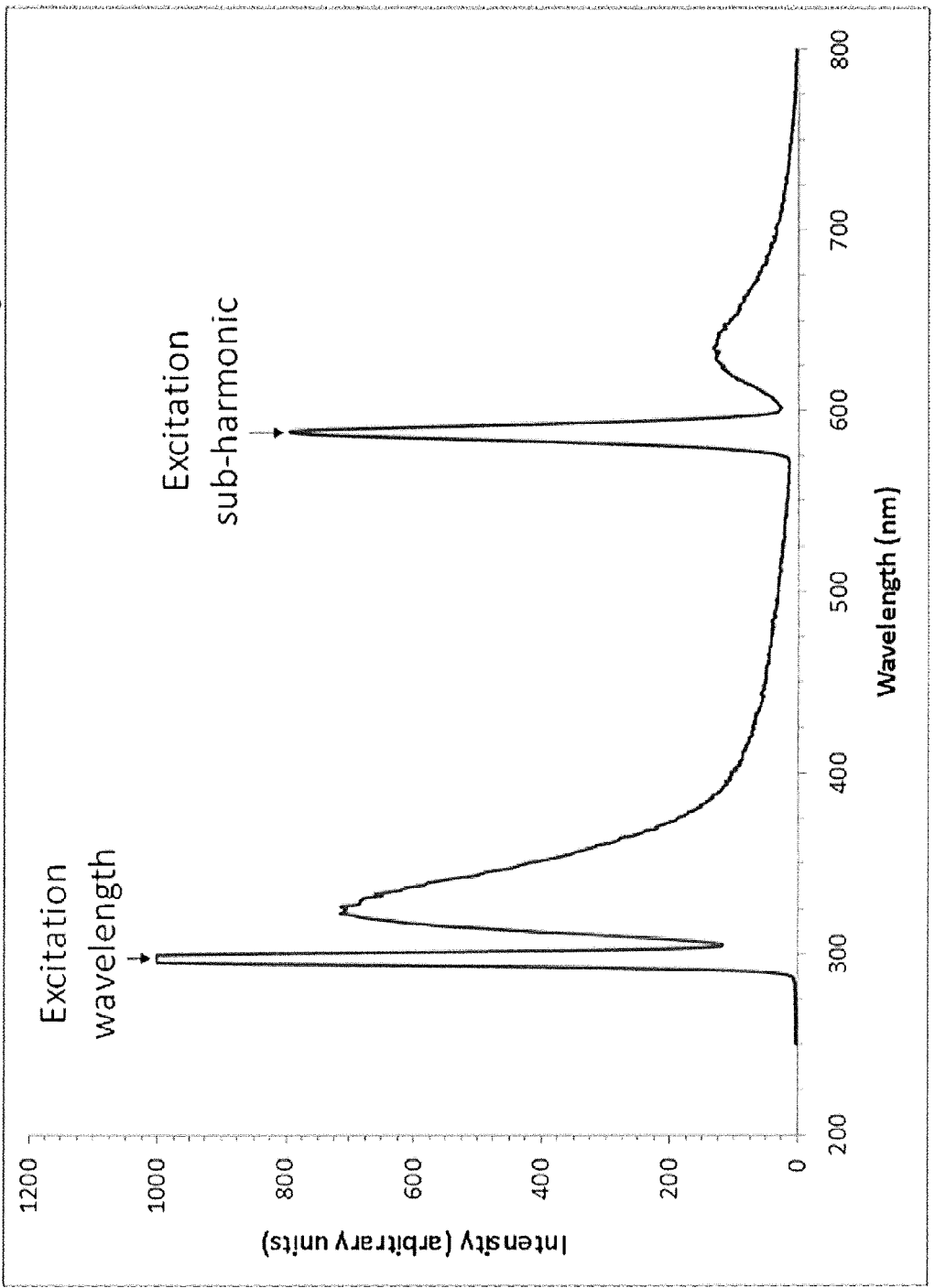
Figure 1. Fluorescence spectra from RbAl(R$_1$)(O$^s$Bu)$_3$ excited with 290 nm wavelength illumination.

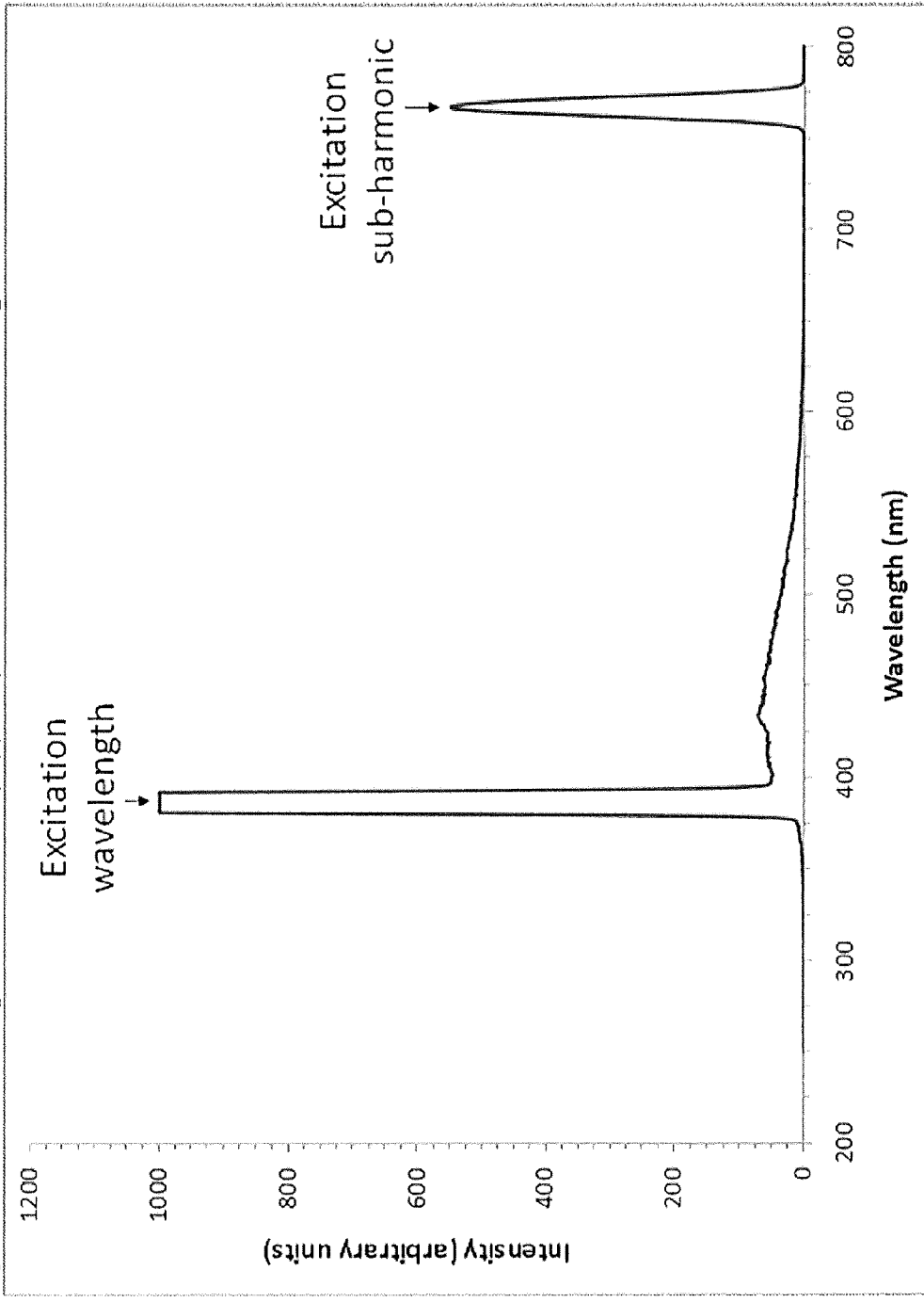
Figure 2. Fluorescence spectra from $RbAl(R_1)(O^sBu)_3$ excited with 380 nm wavelength illumination.
No fluorescence was observed for the Rb-Ti complex below 370 nm excitation wavelength.

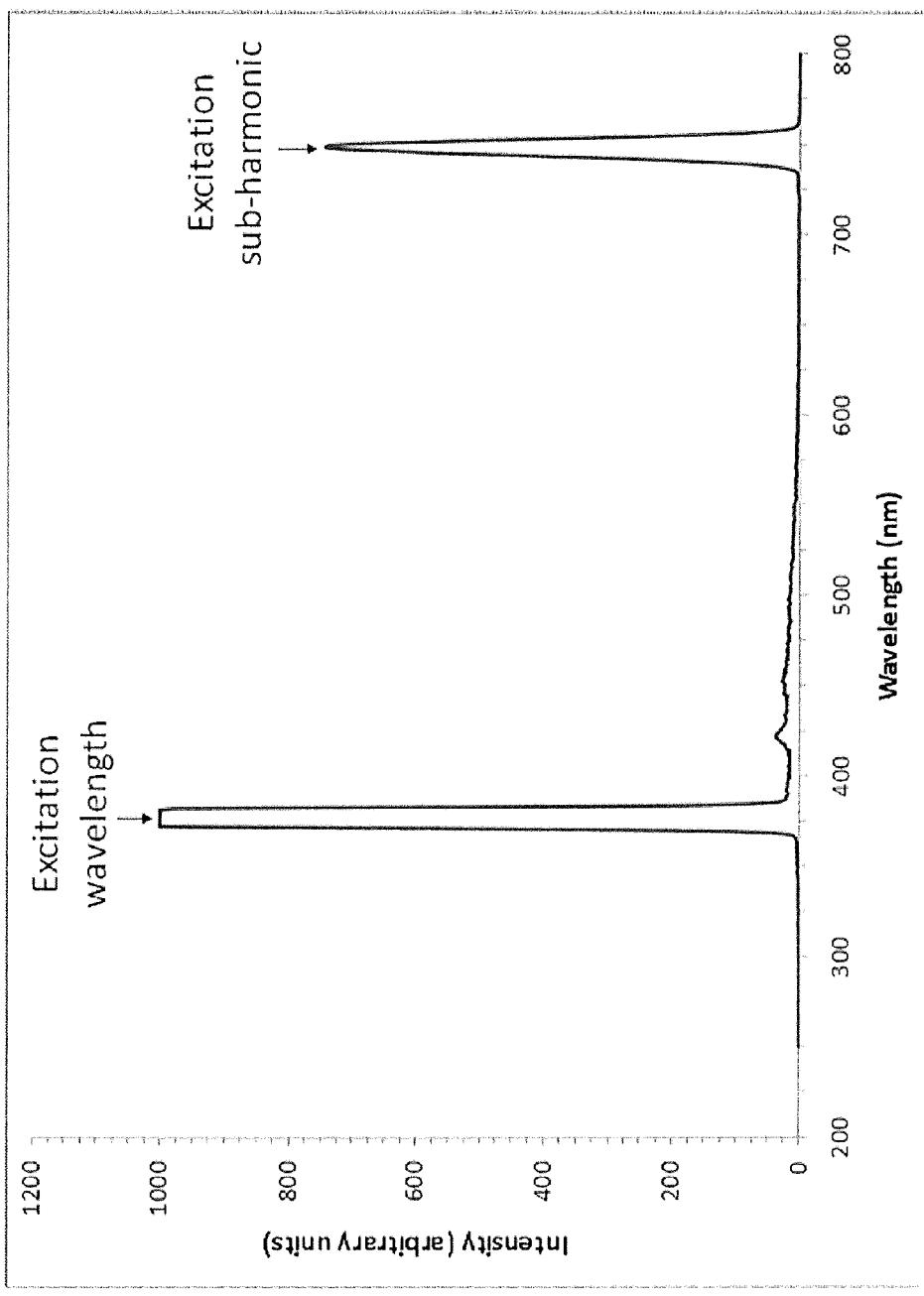
Figure 3a. Fluorescence spectra from RbTi(R$_1$)(OPr)$_4$ complex excited with 370 nm wavelength illumination. A spectrum with the full vertical scale is shown.

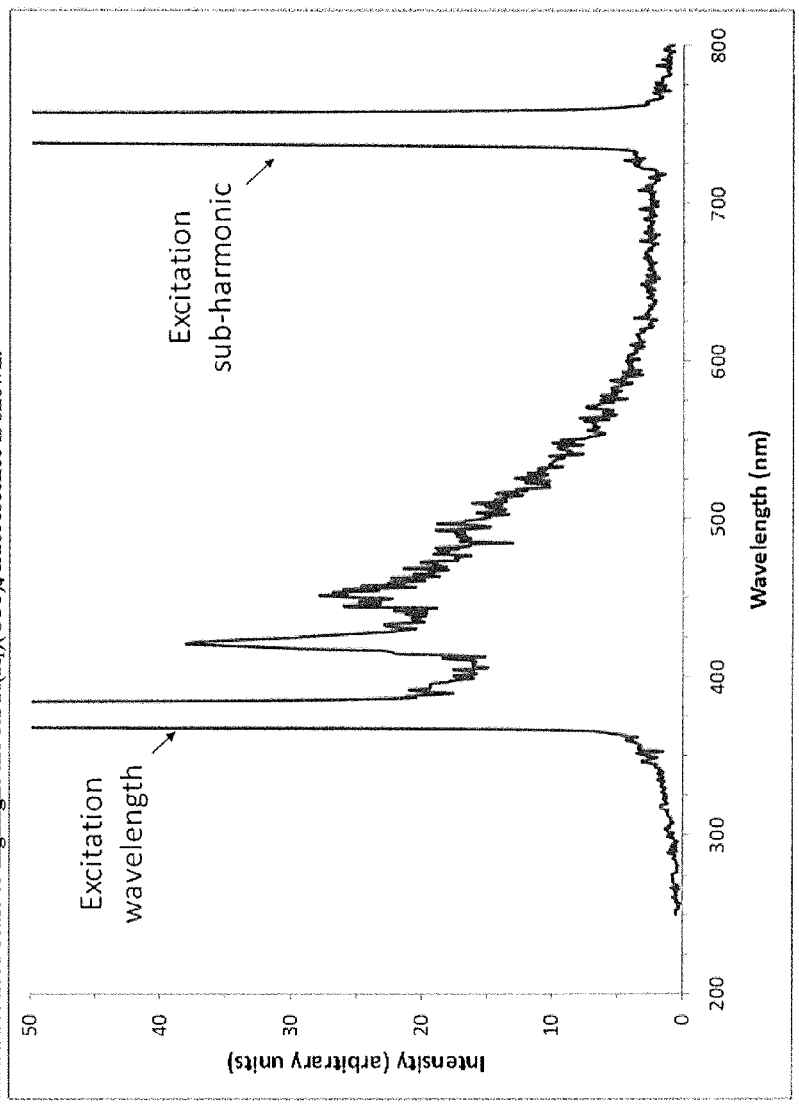
Figure 3b. Fluorescence spectra from RbTi(R₁)(OPr)₄ complex excited with 370 nm wavelength illumination. A spectrum with a reduced scale to highlight the RbTi(R₁)(OPr)₄ fluorescence is shown.

RUBIDIUM AND CESIUM COMPOUNDS FOR TWO-PHOTON ABSORPTION

CROSS REFERENCE TO RELATED APPLICATIONS

The present application hereby claims the benefit of PCT/US2011/053415, filed on Sep. 27, 2011, which claimed benefit of the provisional patent application of the same title, Ser. No. 61/386,687, filed on Sep. 27, 2010, the disclosure of which is hereby incorporated by reference in its entirety.

BACKGROUND

Two-photon absorbing materials are useful for optical applications such as switches, laser amplifiers, and optical down-converters. Rubidium vapor, which has sharp spectral features, has been used or envisioned as a two-photon absorbing material for these applications. However, rubidium vapor may be difficult to use in practice.

Spectral properties of atoms, particularly metals, are extremely sensitive to the environment in which they are placed. It is well-known that absorbance and emission spectra of atoms are broadened and shifted by interaction with other atoms. The close interaction of two metal atoms can also lead to quenching of fluorescence properties, again demonstrating a change of spectral properties.

Small nanoparticles may be synthesized with a single lanthanide metal atom at the center, with a screening set of transition metal atoms, as depicted in FIG. 1 of *Japanese Journal of Applied Physics* 46, pp L83-L85 (2007), see also U.S. Pat. No. 7,695,641).

Fluorescence measurements performed on these nanoparticles show the emission spectrum of the Eu atom to be very narrow, even when the nanoparticles are incorporated into a polymer at high loading. This indicates that the Eu atoms remain isolated by the surrounding Al and O atoms.

The drawback to these nanoparticles is that the electronic isolation of the central Eu atom in high concentrations is presumed to be dependent on the coordination of the Eu (or other lanthanide) by the six oxygen atoms.

BRIEF SUMMARY

In one embodiment, a material which electronically isolates a rubidium or cesium atom, which is bonded to only one or two oxygen atoms. This electronic isolation is manifested in narrow photoluminescence emission spectral peaks.

In another embodiment, an alkali metal compound comprises the empirical formula: $AM(R_1)(OR))_x$; where A is selected from Rb and Cs; M is selected from Al, Ti and V; each R is an independently selected alkyl or aryl group, $R_1$ is selected from alkyl alcohol, aryl alcohol, or a carboxyl group, where OR and $R_1$ are not the same, and x is 2, 3, or 4.

In another embodiment, an optical device, wherein the device comprises a compound selected from: an alkali metal compound comprising the empirical formula: $AM(R_1)(OR)_x$; where A is selected from Rb and Cs; M is selected from Al, Ti and V; each R is an independently selected alkyl or aryl group, and x is 2, 3, or 4; or

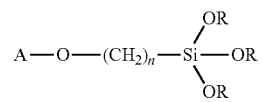

where A is selected from Rb and Cs; each R is an independently selected alkyl or aryl group, and may join to form a ring; and n is an integer from 1 to 50; where the optical device is a toroid or Mach-Zehnder interferometer.

These and other objects and advantages shall be made apparent from the accompanying drawings and the description thereof.

BRIEF DESCRIPTION OF THE FIGURES

The accompanying drawings, which are incorporated in and constitute a part of this specification, illustrate embodiments, and together with the general description given above, and the detailed description of the embodiments given below, serve to explain the principles of the present disclosure.

FIG. 1 is the fluorescence spectrum of $RbAl(R_1)(O^sBu)_3$ excited with 290 nm wavelength illumination.

FIG. 2 is the fluorescence spectrum of $RbAl(R_1)(O^sBu)_3$ excited with 380 nm wavelength illumination.

FIG. 3 is the fluorescence spectrum of $RbTi(R_1)(OPr)_4$ complex excited with 370 nm wavelength illumination.

DETAILED DESCRIPTION

Figure 4:
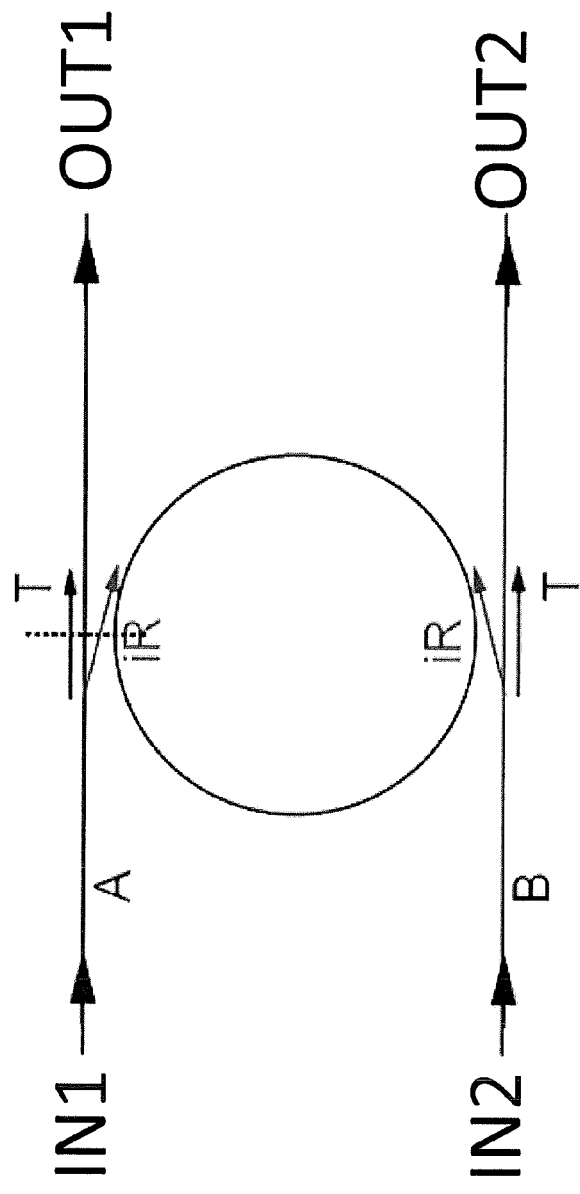
FIG. 4 is a schematic of a toroidal resonator optical device.

In one embodiment, an alkali metal compound comprises the empirical formula: $AM(R_1)(OR)_x$; where A is selected from Rb and Cs; M is selected from Al, Ti and V; each R is an independently selected alkyl or aryl group, $R_1$ is selected from alkyl alcohol, aryl alcohol, or a carboxyl group, where OR and $R_1$ are not the same, and x is 2, 3, or 4. The $R_1$ group may be selected from alkyl alcohol or aryl alcohol. The alkali metal compound may act as a two-photon absorbing material with reduced or no quenching of the vapor-phase fluorescent properties when placed into a condensed phase.

In one embodiment the alkali metal compound has the formula: $RbAl(R_1)(O^sbutyl)_x$, where x is 2, 3, or 4, and $R_1$ is not sec-butyl. In another embodiment the alkali metal compound has the formula: $RbTi(R_1)(O-propyl)_x$, where x is 2, 3, or 4, and $R_1$ is not propyl alcohol. The chemical structure of the alkali metal compound may be formula (1):

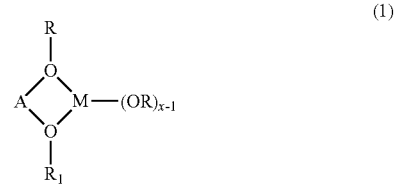

The alkali metal compound may be formed by drying a metal carboxylate so that it is anhydrous. The metal carboxylate may be dissolved in a solvent. A metal alkoxide is then added to the metal carboxylate and heated.

Typical metal carboxylates are rubidium acetate and cesium acetate. However, other carobxylates may be used in place of acetate, such as propanoate, butanoate, or other alkanoates. The metal of the metal carboxylate is selected from rubidium and cesium.

The metal alkoxide may be Ti(OPr)$_4$, Al(O$^s$Bu)$_3$, or vanadium alkoxide. The metal alkoxides that do not work are aluminum isopropoxide and aluminum tert-butoxide. The metals may be selected from Ti, Al, and V.

The solvent may be PGME (propylene glycol monomethyl ether (1-methoxy-2-propanol)). Other solvents may also be useful. In one embodiment the solvent is involved in the formation of the alkali metal compound and is R$_1$. In another embodiment, an alcohol solvent may be useful.

In one embodiment, an all-optical device is a toroid or Mach-Zehnder interferometer, wherein the device comprises an alkali metal compound comprising the empirical formula: AM(R$_1$)(OR)$_x$; where A is selected from Rb and Cs; M is selected from Al, Ti and V; each R is an independently selected alkyl or aryl group, R$_1$ is selected from alkyl alcohol, aryl alcohol, or a carboxyl group, where OR and R$_1$ are not the same, and x is 2, 3, or 4. The R$_1$ group may be selected from alkyl alcohol or aryl alcohol. The alkali metal compound may be deposited onto the surface of the optical device. The alkali metal compound may associate with silica or polymer surfaces to form a thin to monolayer film of the compound. Alternately, the alkali metal compound may be combined with a monomer or polymer to form the coating on the optical device.

There is a desire for active optical devices that have low optical loss and are all-optically controlled. One class of devices is hybrid optical devices, which use a primary material (such as silica) to transport the photons with a secondary material which possesses the appropriate stimuli-sensitive optical response. In many cases, this secondary material interacts with the evanescent optical field to alter the effective optical properties of the device.

There are many possible architectures for these hybrid devices, such as the toroidal resonator shown in FIG. 5. The circle is the resonator structure, which can be created by many different methods. The straight lines representing waveguides or other structures to guide light to and from the resonator. The evanescent wave of the resonator is in contact with secondary material. IN1 and IN2 are incident from the left, while OUT1 and OUT2 are the transmitted fields propagating to the right.

One method to control the function of the resonator is through the use of a two-photon absorbing material. In a simple example of operation, two distinct wavelengths, λA and λB, are incident on the resonator. If the active material has strong absorption for the λA plus λB state, while the absorption is weak for the λA plus λA state, the resonator can be designed so the light with wavelength λA is output through one channel when λB is not present, and is output through the other channel when λB is present. This allows the presence or absence of one beam of light to control the output path taken by a second beam of light, which corresponds to the operation of an all-optical switch.

There are several classes of secondary materials that can be used to fabricate hybrid optical devices. For all-optically controlled devices, it is essential that the secondary material have the following properties: (1) low optical loss at λA and λB, (2) weak two-photon absorption for λA plus λA (3) strong two-photon absorption for λA plus λB, and (4) enables a scalable approach that can be readily manufactured and integrated into more complex structures. Gas vapors have been shown to meet the first three requirements, but are not scalable or easily integrated with other electronic devices. Low optical loss polymers, composites, and sol-matrices that can meet the fourth requirement, but cannot meet the second and third requirements. The materials described herein can satisfy all four conditions.

Wavelengths λA and λB are normally such that the sum of their energies are slightly larger than the energy of the first absorption. For a compound that absorbs strongly at 400 nm, for example, λA and λB may be 730 and 760 nm for example. These wavelengths will not come out of a simple fluorescence measurement, but must be determined from a two-photon absorption experiment.

In one embodiment, the device would use a condensed phase optical material. The requirements for narrow two-photon absorption cannot be met by any material which has broad optical spectra, such as is found in organic materials, or by directly incorporating rubidium or cesium atoms into a condensed phase, such as a sol-gel or a glass.

In one embodiment, a silanated alkali metal alkoxide compound comprising formula 2, where A is selected from Rb and Cs; each R is an independently selected alkyl or aryl group, and may join to form a ring; and n is an integer from 1 to 50.

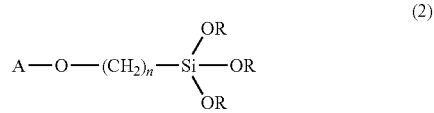

(2)

Silanated alkali metal alkoxide compounds of formula 2 may be deposited onto the surface of an optical device. The silane may associate with silica or polymer surfaces to form a thin to monolayer film of the silanated rubidium compound.

Molecular cages may be used to contain different types of small molecules, such as in Liu, et. al., Angew. Chem. Int. Ed. 2006, 45, 901-904, where a molecular cage was synthesized. This cage was shown to be able to contain different types of small molecules, such as drugs. These small molecules are contained within the cage solely by steric interactions, with no bonding between the cage and the small molecule. This type of molecular cage structure may be used to contain either single Rb or Cs atoms, or a small Rb or Cs-containing molecule. The molecular cage molecules may be placed onto the device surface, to provide the desired two-photon absorption. The molecular cage would act to shield the Rb or Cs atoms from interacting, but would still allow the Rb or Cs atoms to be held in close proximity to the device surface.

An alkyl group is a straight or branched chain of carbon atoms. It may be substituted with functional groups such as alcohols, amines, aryl groups, carboxylic acids, amides, alkenes, and alkynes. Examples of alkyl groups without substitution are methyl, ethyl, propyl, iso-propyl, s-butyl, iso-butyl, tert-butyl.

An aryl group is a substituent with aromatic characteristics. Examples include phenyl, 4-t-butylphenyl, 2,4,6-trimethylphenyl, naphthyl. Aryl groups may be substituted with alkyl groups.

While the present disclosure has illustrated by description several embodiments and while the illustrative embodiments have been described in considerable detail, it is not the intention of the applicant to restrict or in any way limit the scope of the appended claims to such detail. Additional advantages and modifications may readily appear to those skilled in the art. In particular, there are many alternate methods to incorporate a rubidium or cesium atom into a molecular cage, to potentially provide electronic isolation to the atom resulting in a narrow two-photon absorption.

EXAMPLES

Example 1

Synthesis of both $RbTi(R_1)(OR)_4$ and $RbAl(R_1)(O^sBu)_2$

In a typical synthesis for $RbTi(R_1)(OPr)_4$, 9.76 mmol rubidium acetate was dehydrated in a round-bottomed flask, which was heated under vacuum in a 150° C. oil bath (need only be 120° C.) for more than 2 hours. The flask was then cooled slightly and purged with Ar before adding any reactant. An alkoxide solution was prepared by dissolving 9.76 mmol $Ti(OPr)_4$ in 9.1 g PGME (propylene glycol monomethyl ether (1-methoxy-2-propanol)). The alkoxide solution was then injected into the cooled flask. The mixed solution was refluxed for 1 hour under Ar. A clear yellowish solution was obtained after the reaction. $RbAl(R_1)(O^sBu)_3$ was synthesized with the same procedure using $Al(O^sBu)_3$.

Example 1a

Synthesis of the compound was attempted using two alternative aluminum metal-organic precursors: aluminum isopropoxide and aluminum tert-butoxide. The procedures for these experiments were the same as with the aluminum tri-sec-butoxide with the appropriate molar quantity of the alternative aluminum precursor added. In both cases these reactions failed. Neither the aluminum isopropoxide nor the aluminum tert-butoxide were soluble in the PGME solvent and there was visible residue on the bottom of the flask after the reaction.

Alternative solvent systems were also tried in an effort to determine if this synthesis could be carried out in other solvents; toluene and tetrahydrofuran (THF) were used. In both cases the Rb-acetate dissolved in the solvent as did the Al-tri-sec-butoxide. However, after the reaction was complete the solution was discolored (yellowish for toluene and a brown color for the THF) and therefore no further experiments were undertaken with these solvents.

Example 2

Photoluminescence evaluation of $RbAl(R_1)(O^sBu)_3$

Measurements of solutions were performed using a Varian Cary Eclipse Fluorescence Spectrophotometer. The photoluminescence emission spectrum of $RbAl(R_1)(O^sBu)_3$ excited at 290 nm and 380 nm is shown in FIGS. 1 and 2.

Prophetic Example 3

Silanated Rubidium Alkoxide Compound

The silanated rubidium compound of formula 2 may be synthesized according to the following reaction scheme:

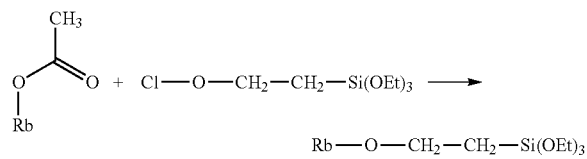

Both starting materials are available.

What is claimed is:

1. An alkali metal compound comprising the empirical formula:
   $AM(R_1)(OR)_x$; where A is selected from Rb and Cs; M is selected from Al, Ti and V;
   each R is independently selected from sec-butyl or propyl, $R_1$ is selected from alkyl alcohol, aryl alcohol, or a carboxyl group, where OR and $R_1$ are not the same, and x is 2, 3, or 4.

2. The alkali metal of claim 1, wherein A is Rb.

3. The alkali metal of claim 1, wherein M is Ti.

4. The alkali metal of claim 1, wherein $R_1$ is propylene glycol monomethyl ether.

5. The alkali metal of claim 1, wherein $R_1$ is acetate.

6. An alkali metal compound formed by the process of: drying a metal carboxylate in a solvent, adding a metal alkoxide, and heating the mixture; where the metal of the metal carboxylate is Rb or Cs, and where the metal alkoxide is Al alkoxide, Ti alkoxide, or V alkoxide.

7. The alkali metal compound of claim 6, where the metal of the metal carboxylate comprises rubidium acetate or cesium acetate.

8. The alkali metal compound of claim 6, where the metal of the metal carboxylate is Rb.

9. The alkali metal compound of claim 6, where the metal alkoxide is titanium propoxide.

10. The alkali metal compound of claim 6, where the solvent is propylene glycol monomethyl ether.

11. An optical device, wherein the device comprises a compound selected from:
    an alkali metal compound comprising the empirical formula: $AM(R_1)(OR)_x$; where A is selected from Rb and Cs; M is selected from Al, Ti and V; each R is an independently selected alkyl or aryl group, $R_1$ is selected from alkyl alcohol, aryl alcohol, or a carboxyl group, where OR and $R_1$ are not the same, and x is 2, 3, or 4; or

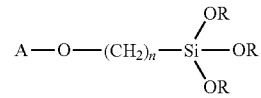

where A is selected from Rb and Cs; each R is an independently selected alkyl or aryl group, and may join to form a ring; and n is an integer from 1 to 50;
where the optical device is a toroid or Mach-Zehnder interferometer.

12. The optical device of claim 11, wherein the compound is an alkali metal compound comprising the empirical formula: $AM(R_1)(OR)_x$; where A is selected from Rb and Cs; M is selected from Al, Ti and V; each R is an independently selected alkyl or aryl group, $R_1$ is selected from alkyl alcohol, aryl alcohol, or a carboxyl group, where OR and $R_1$ are not the same, and x is 2, 3 or 4.

13. The optical device of claim 11, wherein A is Rb.

14. The optical device of claim 11, wherein R is sec-butyl.

15. The optical device of claim 11, wherein M is Ti.

16. The optical device of claim 11, wherein R is propyl.

17. The optical device of claim 11, wherein the device is capable of all-optical switching, where the presence of two optical beams with distinct wavelengths alters the optical properties of the material from the optical properties that exist when either optical beam is there individually.

18. The optical device of claim 11, wherein the change in the optical properties of the material allow the device to alter the path by which the light exits the device.

19. An alkali metal compound comprising the empirical formula: $AM(R_1)(OR)_x$; where A is selected from Rb and Cs; M is selected from Al, Ti and V; each R is an independently selected alkyl or aryl group, $R_1$ is selected from propylene glycol monomethyl ether or acetate, where OR and $R_1$ are not the same, and x is 2, 3, or 4.

20. The alkali metal of claim 19, wherein A is Rb.

21. The alkali metal of claim 19, wherein M is Ti.

* * * * *